(12) United States Patent
Amano et al.

(10) Patent No.: US 8,383,588 B2
(45) Date of Patent: Feb. 26, 2013

(54) FIBROSIS INHIBITOR FOR IMPLANTED ORGAN

(75) Inventors: Jun Amano, Matsumoto (JP); Ken-ichi Ito, Matsumoto (JP); Kazuhiro Yamaura, Saku (JP); Kunio Matsumoto, Ibaraki (JP); Toshikazu Nakamura, Kyoto (JP)

(73) Assignee: Kringle Pharma Inc., Osaka (JP)

( * ) Notice: Subject to any disclaimer, the term of this patent is extended or adjusted under 35 U.S.C. 154(b) by 0 days.

(21) Appl. No.: 13/288,392

(22) Filed: Nov. 3, 2011

(65) Prior Publication Data

US 2012/0149642 A1 Jun. 14, 2012

Related U.S. Application Data

(62) Division of application No. 12/695,532, filed on Jan. 28, 2010, now Pat. No. 8,076,289, which is a division of application No. 11/795,314, filed as application No. PCT/JP2005/016653 on Sep. 9, 2005, now Pat. No. 7,696,170.

(30) Foreign Application Priority Data

Jan. 24, 2005 (JP) ................................ 2005-016191

(51) Int. Cl.
*A61K 38/18* (2006.01)
(52) U.S. Cl. ...................................... 514/9.5
(58) Field of Classification Search .................. None
See application file for complete search history.

(56) References Cited

U.S. PATENT DOCUMENTS

| | | | |
|---|---|---|---|
| 5,776,464 | A | 7/1998 | Nakamura et al. |
| 6,099,841 | A | 8/2000 | Hilian et al. |
| 6,699,837 | B2 | 3/2004 | Nakamura et al. |
| 7,563,768 | B2 | 7/2009 | Nakamura et al. |

FOREIGN PATENT DOCUMENTS

| | | |
|---|---|---|
| EP | 1 036 566 | 9/2000 |
| JP | 7-258111 | 10/1995 |
| JP | 7-300426 | 11/1995 |
| JP | 10-194986 | 7/1998 |
| JP | 2000-239182 | 9/2000 |
| WO | 96/40914 | 12/1996 |
| WO | 01/26694 | 4/2001 |
| WO | 02/05840 | 1/2002 |

OTHER PUBLICATIONS

H. Tashiro et al., "Hepatocyte Growth Factor Prevents Chronic Allograft Dysfunction in Liver-Transplanted Rats", *Transplantation*, vol. 76, No. 5, pp. 761-765, Sep. 15, 2003.
K. Yamaura et al., "Suppression of Acute and Chronic Rejection by Hepatocyte Growth Factor in a Murine Model of Cardiac Transplantation", *Circulation*, vol. 110, No. 12, pp. 1650-1657, published on the internet on Sep. 13, 2004 at http://circ.ahajournals.org/.
K. Yamaura et al., "Suppression of Acute and Chronic Rejection by Hepatocyte Growth Factor in a Murine Model of Cardiac Transplantation", *Circulation*, vol. 110, No. 12, pp. 1650-1657, Sep. 21, 2004.
Y. Isaka et al., "Electroporation-mediated HGF gene transfection protected the kidney against graft injury", *Gene Therapy* (2005), vol. 12, No. 10, pp. 815-820.
I. Herrero-Fresneda et al., "HGF gene therapy attenuates renal allograft scarring by preventing the profibrotic inflammatory-induced mechanisms", *Kidney International Society of Nephrology* (2006), vol. 70, No. 2, pp. 265-274.
S. Mizuno et al., "Hepatocyte growth factor prevents renal fibrosis and dysfunction in a mouse model of chronic renal disease", *The Journal of Clinical Investigation* (1998), vol. 101, No. 9, pp. 1827-1834.
K. Yazawa et al., "Direct transfer of hepatocyte growth factor gene into kidney suppresses cyclosporine A nephrotoxicity in rats", *Nephrology Dialysis Transplantation* (2004), vol. 19, No. 4, pp. 812-816.

*Primary Examiner* — Marianne P Allen
(74) *Attorney, Agent, or Firm* — Wenderoth, Lind & Ponack, L.L.P.

(57) ABSTRACT

A pharmaceutical preparation comprising a hepatocyte growth factor or a DNA molecule encoding the same and the like according to the present invention can suppress the fibrosis of a transplanted organ after organ transplantation. The present invention is useful in the fields of organ transplantation and regeneration therapy.

3 Claims, 1 Drawing Sheet

SEQUENCE LISTING

```
<160> NUMBER OF SEQ ID NOS: 4

<210> SEQ ID NO 1
<211> LENGTH: 728
<212> TYPE: PRT
<213> ORGANISM: Homo sapiens

<400> SEQUENCE: 1

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
```

```
                145                 150                 155                 160
Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
                180                 185                 190

Asn Pro Glu Val Arg Tyr Glu Val Cys Asp Ile Pro Gln Cys Ser Glu
                195                 200                 205

Val Glu Cys Met Thr Cys Asn Gly Glu Ser Tyr Arg Gly Leu Met Asp
                210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
                275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
                340                 345                 350

Tyr Cys Arg Asn Pro Asp Gly Ser Glu Ser Pro Trp Cys Phe Thr Thr
                355                 360                 365

Asp Pro Asn Ile Arg Val Gly Tyr Cys Ser Gln Ile Pro Asn Cys Asp
                370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
                420                 425                 430

Ser Lys Leu Asn Glu Asn Tyr Cys Arg Asn Pro Asp Asp Asp Ala His
                435                 440                 445

Gly Pro Trp Cys Tyr Thr Gly Asn Pro Leu Ile Pro Trp Asp Tyr Cys
                450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
                500                 505                 510

Tyr Arg Asn Lys His Ile Cys Gly Gly Ser Leu Ile Lys Glu Ser Trp
                515                 520                 525

Val Leu Thr Ala Arg Gln Cys Phe Pro Ser Arg Asp Leu Lys Asp Tyr
                530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575
```

```
Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 2
<211> LENGTH: 723
<212> TYPE: PRT
<213> ORGANISM: Homo sapiens

<400> SEQUENCE: 2

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
    210                 215                 220
```

-continued

```
Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
            245                 250                 255

Asn Pro Asp Gly Gln Pro Arg Pro Trp Cys Tyr Thr Leu Asp Pro His
        260                 265                 270

Thr Arg Trp Glu Tyr Cys Ala Ile Lys Thr Cys Ala Asp Asn Thr Met
    275                 280                 285

Asn Asp Thr Asp Val Pro Leu Glu Thr Thr Glu Cys Ile Gln Gly Gln
290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
            340                 345                 350

Asp Gly Ser Glu Ser Pro Trp Cys Phe Thr Thr Asp Pro Asn Ile Arg
        355                 360                 365

Val Gly Tyr Cys Ser Gln Ile Pro Asn Cys Asp Met Ser His Gly Gln
    370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415

Leu His Arg His Ile Phe Trp Glu Pro Asp Ala Ser Lys Leu Asn Glu
            420                 425                 430

Asn Tyr Cys Arg Asn Pro Asp Asp Asp Ala His Gly Pro Trp Cys Tyr
        435                 440                 445

Thr Gly Asn Pro Leu Ile Pro Trp Asp Tyr Cys Pro Ile Ser Arg Cys
    450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Ile Gly Trp Met Val Ser Leu Arg Tyr Arg Asn Lys His
            500                 505                 510

Ile Cys Gly Gly Ser Leu Ile Lys Glu Ser Trp Val Leu Thr Ala Arg
        515                 520                 525

Gln Cys Phe Pro Ser Arg Asp Leu Lys Asp Tyr Glu Ala Trp Leu Gly
    530                 535                 540

Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
                565                 570                 575

Met Lys Leu Ala Arg Pro Ala Val Leu Asp Asp Phe Val Ser Thr Ile
            580                 585                 590

Asp Leu Pro Asn Tyr Gly Cys Thr Ile Pro Glu Lys Thr Ser Cys Ser
        595                 600                 605

Val Tyr Gly Trp Gly Tyr Thr Gly Leu Ile Asn Tyr Asp Gly Leu Leu
    610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
                645                 650                 655
```

```
Glu Lys Ile Gly Ser Gly Pro Cys Glu Gly Asp Tyr Gly Gly Pro Leu
            660                 665                 670

Val Cys Glu Gln His Lys Met Arg Met Val Leu Gly Val Ile Val Pro
        675                 680                 685

Gly Arg Gly Cys Ala Ile Pro Asn Arg Pro Gly Ile Phe Val Arg Val
    690                 695                 700

Ala Tyr Ala Lys Trp Ile His Lys Ile Ile Leu Thr Tyr Lys Val
705                 710                 715                 720

Pro Gln Ser

<210> SEQ ID NO 3
<211> LENGTH: 2187
<212> TYPE: DNA
<213> ORGANISM: Homo sapiens

<400> SEQUENCE: 3
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa     180
accaaaaaag tgaatactgc agaccaatgt gctaatagat gtactaggaa taaggactt      240 ccattcactt gcaaggcttt tgttttgat aaagcaagaa acaatgcct ctggttcccc       300 ttcaatagca tgtcaagtgg agtgaaaaaa gaatttggcc atgaatttga cctctatgaa     360
aacaaagact acattagaaa ctgcatcatt ggtaaggac gcagctacaa gggaacagta     420
tctatcacta gagtggcat caaatgtcag ccctggagtt ccatgatacc acgaacac       480 agcttttgc cttcgagcta tcggggtaaa gacctacagg aaaactactg tcgaaatcct     540
cgaggggaag aaggggggacc ctggtgtttc acaagcaatc cagaggtacg ctacgaagtc    600
tgtgacattc ctcagtgttc agaagttgaa tgcatgacct gcaatgggga gagttatcga    660
ggtctcatgg atcatacaga atcaggcaag atttgtcagc gctgggatca tcagacacca    720
caccggcaca aattcttgcc tgaaagatat cccgacaagg gcttttgatga taattattgc   780 cgcaatcccg atggccagcc gaggccatgg tgctatactc ttgaccctca cacccgctgg    840
gagtactgtg caattaaaac atgcgctgac aatactatga atgacactga tgttcctttg    900
gaaacaactg aatgcatcca aggtcaagga gaaggctaca ggggcactgt caataccatt    960
tggaatggaa ttccatgtca gcgttgggat tctcagtatc ctcacgagca tgacatgact   1020
cctgaaaatt tcaagtgcaa ggacctacga gaaaattact gccgaaatcc agatgggtct   1080
gaatcaccct ggtgtttac cactgatcca acatccgag ttggctactg ctcccaaatt     1140
ccaaactgtg atatgtcaca tggacaagat tgttatcgtg ggaatggcaa aaattatatg   1200
ggcaacttat cccaaacaag atctggacta acatgttcaa tgtgggacaa gaacatggaa   1260
gacttacatc gtcatatctt ctgggaacca gatgcaagta agctgaatga aattactgc    1320 cgaaatccag atgatgatgc tcatggaccc tggtgctaca gggaaatcc actcattcct    1380 tgggatttatt gccctatttc tcgttgtgaa ggtgatacca cacctacaat agtcaattta   1440
gaccatcccg taatatcttg tgccaaaacg aaacaattgc gagttgtaaa tgggattcca   1500
acacgaacaa acataggatg gatggttagt ttgagataca gaatacaa tatctgcgga    1560 ggatcattga taaaggagag ttgggttctt actgcacgac agtgtttccc ttctcgagac   1620
ttgaaagatt atgaagcttg gcttggaatt catgatgtcc acggaagagg agatgagaaa   1680
tgcaaacagg ttctcaatgt ttcccagctg gtatatggcc ctgaaggatc agatctggtt   1740
```

```
ttaatgaagc ttgccaggcc tgctgtcctg gatgattttg ttagtacgat tgatttacct    1800
aattatggat gcacaattcc tgaaaagacc agttgcagtg tttatggctg gggctacact    1860
ggattgatca actatgatgg cctattacga gtggcacatc tctatataat gggaaatgag    1920
aaatgcagcc agcatcatcg agggaaggtg actctgaatg agtctgaaat atgtgctggg    1980
gctgaaaaga ttggatcagg accatgtgag ggggattatg gtggcccact tgtttgtgag    2040
caacataaaa tgagaatggt tcttggtgtc attgttcctg gtcgtggatg tgccattcca    2100
aatcgtcctg gtattttgt ccgagtagca tattatgcaa aatggataca caaaattatt    2160
ttaacatata aggtaccaca gtcatag                                        2187
```

<210> SEQ ID NO 4
<211> LENGTH: 2172
<212> TYPE: DNA
<213> ORGANISM: Homo sapiens
<400> SEQUENCE: 4

```
atgtgggtga ccaaactcct gccagccctg ctgctgcagc atgtcctcct gcatctcctc      60
ctgctcccca tcgccatccc ctatgcagag ggacaaagga aaagaagaaa tacaattcat     120
gaattcaaaa atcagcaaa gactacccta atcaaaatag atccagcact gaagataaaa     180
accaaaaaag tgaatactgc agaccaatgt gctaatagat gtactaggaa taaggactt     240 ccattcactt gcaaggcttt tgtttttgat aaagcaagaa acaatgccct tggttcccc     300 ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta gagtggcat caaatgtcag ccctggagtt ccatgatacc acacgaacac     480
agctatcggg gtaaagacct acaggaaaac tactgtcgaa atcctcgagg ggaagaaggg     540 ggacctggt gtttcacaag caatccagag gtacgctacg aagtctgtga cattcctcag     600
tgttcagaag ttgaatgcat gacctgcaat ggggagagtt atcgaggtct catggatcat     660
acagaatcag gcaagatttg tcagcgctgg gatcatcaga caccacaccg gcacaaattc     720
ttgcctgaaa gatatcccga caagggcttt gatgataatt attgccgcaa tcccgatggc     780
cagccgaggc catggtgcta tactcttgac cctcacaccc gctgggagta ctgtgcaatt     840
aaaacatgcg ctgacaatac tatgaatgac actgatgttc ctttggaaac aactgaatgc     900
atccaaggtc aaggagaagg ctacaggggc actgtcaata ccattgagaa tggaattcca     960
tgtcagcgtt gggattctca gtatcctcac gagcatgaca tgactcctga aaatttcaag    1020
tgcaaggacc tacgagaaaa ttactgccga atccagatg gtctgaatc accctggtgt    1080 tttaccactg atccaaacat ccgagttggc tactgctccc aaattccaaa ctgtgatatg    1140
tcacatggac aagattgtta tcgtgggaat ggcaaaaatt atatgggcaa cttatcccaa    1200
acaagatctg gactaacatg ttcaatgtgg acaagaacaa tggaagactt acatcgtcat    1260
atcttctggg aaccagatgc aagtaagctg aatgagaatt actgccgaaa tccagatgat    1320
gatgctcatg gaccctggtg ctacacggga aatccactca ttccttggga ttattgcccct    1380 atttctcgtt gtgaaggtga taccacacct acaatagtca atttagacca tcccgtaata    1440
tcttgtgcca aaacgaaaca attgcgagtt gtaaatggga ttccaacacg aacaaacata    1500
ggatggatgg ttagtttgag atacagaaat aaacatatct gcggaggatc attgataaag    1560
gagagttggg ttcttactgc acgacagtgt ttccctctc gagacttgaa agattatgaa    1620
gcttggcttg gaattcatga tgtccacgga agaggagatg agaaatgcaa acaggttctc    1680
```

```
aatgtttccc agctggtata tggccctgaa ggatcagatc tggttttaat gaagcttgcc    1740
aggcctgctg tcctggatga ttttgttagt acgattgatt tacctaatta tggatgcaca    1800
attcctgaaa agaccagttg cagtgtttat ggctggggct acactggatt gatcaactat    1860
gatggcctat tacgagtggc acatctctat ataatgggaa atgagaaatg cagccagcat    1920
catcgaggga aggtgactct gaatgagtct gaaatatgtg ctggggctga aaagattgga    1980
tcaggaccat gtgagggga ttatggtggc ccacttgttt gtgagcaaca taaaatgaga    2040
atggttcttg gtgtcattgt tcctggtcgt ggatgtgcca ttccaaatcg tcctggtatt    2100
tttgtccgag tagcatatta tgcaaaatgg atacacaaaa ttattttaac atataaggta    2160
ccacagtcat ag                                                        2172
```

FIBROSIS INHIBITOR FOR IMPLANTED ORGAN

This application is a Divisional of U.S. application Ser. No. 12/695,532, filed Jan. 28, 2010, now issued as U.S. Pat. No. 8,076,289, which is a Divisional of U.S. application Ser. No. 11/795,314, filed Oct. 4, 2007, now issued as U.S. Pat. No. 7,696,170, which is a national stage application of International application No. PCT/JP2005/016653, filed Sep. 9, 2005.

TECHNICAL FIELD

The present invention relates to a medicinal drug comprising a hepatocyte growth factor (hereinafter referred to briefly as "HGF"), which acts to suppress the fibrosis of a transplanted organ as caused by the long-term administration of an immunosuppressive drug. And the present invention is also concerned with an immunologic-tolerance drug comprising, among HGF, HGF having 5 amino acids deleted, which drug can permit the recipient patient to acquire immunologic tolerance.

BACKGROUND ART

Organ transplantation has come to be established as a sort of medical practice where no therapy is available other than organ replacement. In recent years, however, a currently increased number of organ transplant survival and a follow-up survey of transplant recipients, or the patients each having had an organ transplanted, reveal that there is arising the problem of greater concern in that the transplanted organs have been undergoing gradual fibrosis with an elapse of a prolonged period of time after the organ transplantation. In the organ transplantation, immunosuppressive drugs are used, for example, to suppress rejection of the transplanted grafts or the transplanted tissues, and must continue to be taken by the patients throughout their lifetime, except in the case of autografts or isografts. The fibrosis of a transplanted organ is found to develop in the graft-recipient patient who is kept placed on indefinite, continued immunosuppressant regimens. Although the causal relationship between the use of immunosuppressive drugs and the onset of the transplanted organ fibrosis is yet to be clarified, there has not been known so far any means to suppress the fibrosis of transplanted organs in the continued immunosuppressant regimens. It has heretofore been considered necessary for a patient to continue to take the immunosuppressive drugs throughout its lifetime, since such immunosuppressants are essential for the establishment and survival of grafts. Referring particularly to such immunosuppressive drugs, Cyclosporine and FK 506 (Taclolimus), with their potent immunosuppressive activity, have attained excellent performance in suppressing the graft rejection after transplantation of the organs, such as kidney, liver, heart, pancreas, etc., and are attracting increased attention. Namely, Cyclosporine and other immunosuppressive drugs, which can reduce outstandingly the incidence of acute rejection after organ transplantation and find frequent application in organ transplantation, lower the incidence of bone marrow depression, and can offer the advantage that severe infections brought about by a reduced number of leucocytes can be prevented from developing to thereby facilitate the rejection management after organ transplantation to be conducted, thus enabling the survival performance of organ transplantation to be enhanced remarkably. However, such immunosuppressive drugs, Cyclosproin, etc., are also observed to produce side effects or adverse reactions, which include those occurring at sites other than the site of transplantation or systemic ones, such as nephrotoxicity, hepatotoxicity, neuropathy, hypertension, necrosis of caput femoris, cataract, diabetes mellitus, acute pancreatitis, cytomegalovirus infections, etc. It is known that HGH is able to alleviate such systemic side effects caused by the immunosuppressive drugs (refer to the Official Gazette of JP Hei 08-89869 A). HGF is the protein which was discovered by the present inventors, Nakamura et al., to be present in the sera of the regenerated liver of rats with regenerating liver and found to act as a factor capable of proliferating mature hepatocytes in vitro (refer to Biochemical and Biophysical Research Communications, 1984, vol. 122, p. 1450-1459). Furthermore, Nakamura et al. succeeded in isolating HGF from platelets of a rat (refer to Proc. Nat. Acad. Sci., 1986, vol. 83, p. 6489, and FEBS Letters, 1987, vol. 22, p. 311), and identified partly its amino acid sequence. Subsequently, Nakamura et al. conducted cDNA cloning of human and rat HGF on the basis of the amino acid sequence elucidated, and succeeded in producing HGF in the form of a protein through introduction of the resultant cDNA into animal cells by recombinant DNA technology (for example, refer to Nature, 1989, vol. 342, p. 440-443).

DISCLOSURE OF THE INVENTION

The Problem That the Invention is Intended to Solve

The present invention relates to a medicinal drug which acts to suppress the gradually ongoing fibrosis of a transplanted organ and the induction of organ insufficiencies in a recipient patient kept on the continued immunosuppressant regimen. Also, the present invention is concerned with an immunotolerance acquiring agent which can allow a recipient patient to acquire immunologic tolerance against the transplant rejection, when an organ is transplanted from a donor to the recipient.

Means for Solving the Problem

The present inventors found that administration of HGF can result in successful suppression of the fibrosis of a transplanted organ in a recipient animal and that administration of HGF having 5 amino acids deleted allows such recipient animal to acquire immunologic tolerance against the transplanted organ. These findings were followed by further continued research work, leading the present inventors to completion of the present invention.

Thus, the present invention relates to:

(1) An agent for suppressing the fibrosis of a transplanted organ caused by an immunosuppressive drug as administered to a recipient, characterized in that said agent comprises HGF;

(2) The agent for suppressing the fibrosis of a transplanted organ as described above under (1), characterized in that said HGF is a peptide consisting of the amino acid sequence shown in SEQ ID NO: 1 or 2 or comprising substantially the same amino acid sequence as the one shown in SEQ ID NO: 1 or 2, which peptide acts as HGF, or a partial polypeptide thereof which can also function as HGF;

(3) An agent for suppressing the fibrosis of a transplanted organ caused by an immunosuppressive drug as administered to the recipient, characterized in that said agent comprises the DNA molecule encoding HGF;

(4) The agent for suppressing the fibrosis of a transplanted organ as described above under (3), characterized in that the DNA molecule encoding HGF is a DNA molecule consisting of the nucleotide sequence as shown in SEQ ID NO: 3 or 4, or a DNA molecule which hybridizes under stringent conditions with a DNA molecule comprising a nucleotide sequence complementary to the DNA molecule consisting of the nucleotide sequence as shown in SEQ ID NO: 3 or 4 and which encodes a peptide acting as HGF;

(5) The agent for suppressing the fibrosis of a transplanted organ as described above under any one of (1) to (4), characterized in that the immunosuppressive drug is Tacrolimus;

(6) An immunologic tolerance acquiring agent, characterized in that said agent comprises a peptide consisting of the amino acid sequence as shown in SEQ ID NO: 2, a peptide comprising an amino acid sequence being substantially the same as the one as shown in SEQ ID NO: 2 and which peptide acts as HGF, or a partial polypeptide thereof which can also functions as HGF; and (7) An immunologic tolerance acquiring agent, characterized in that said agent comprises the DNA molecule consisting of the nucleotide sequence as shown in SEQ ID NO: 4, or a DNA molecule which hybridizes under stringent conditions with a DNA molecule comprising a nucleotide sequence complementary to the DNA molecule consisting of the nucleotide sequence as shown in SEQ ID NO: 4 and which encodes a peptide acting as HGF.

The present invention also relates to:

(8) A method for suppressing the fibrosis of a transplanted organ, characterized in that said method comprises administering HGF to a mammal having had an organ transplanted which is placed on the immunosuppressive-drug regimen;

(9) The method as described above under (8), characterized in that said HGF is a peptide consisting of the amino acid sequence shown in SEQ ID NO: 1 or 2 or comprising substantially the same amino acid sequence as the one shown in SEQ ID NO: 1 or 2, which peptide acts as HGF, or a partial polypeptide thereof which can also function as HGF;

(10) A method for suppressing the fibrosis of a transplanted organ, characterized in that said method comprises administering a DNA molecule encoding HGF to a mammal having had an organ transplanted which is placed on the immunosuppressive-drug regimen;

(11) The method as described above under (10), characterized in that the DNA molecule encoding HGF is a DNA molecule consisting of the nucleotide sequence as shown in SEQ ID NO: 3 or 4, or a DNA molecule which hybridizes under stringent conditions with a DNA molecule comprising a nucleotide sequence complementary to the DNA molecule consisting of the nucleotide sequence as shown in SEQ ID NO: 3 or 4 and which codes for a peptide acting as HGF;

(12) The method as described above under any one of (8) to (11), characterized in that the immunosuppressive drug is Tacrolimus;

(13) A method for allowing a recipient mammal to acquire immunologic tolerance, characterized in that said method comprises administering to the mammal going to have an organ transplanted a peptide consisting of the amino acid sequence as shown in SEQ ID NO: 2, a peptide comprising an amino acid sequence being substantially the same as the one as shown in SEQ ID NO: 2 and which peptide acts as HGF, or a partial polypeptide thereof which can also functions as HGF; and

(14) A method for allowing a recipient mammal to acquire immunologic tolerance, characterized in that said method comprises administering to a mammal going to have an organ transplanted the DNA molecule consisting of the nucleotide sequence as shown in SEQ ID NO: 4, or a DNA molecule which hybridizes under stringent conditions with a DNA molecule comprising a nucleotide sequence complementary to the DNA molecule consisting of the nucleotide sequence as shown in SEQ ID NO: 4 and which encodes a peptide acting as HGF.

Also, the present invention relates to:

(15) Use of HGF in the manufacture of a medicinal drug for suppressing the fibrosis of a transplanted organ as brought about by administration of an immunosuppressive drug;

(16) The use as described above under (15), characterized in that said HGF is a peptide consisting of the amino acid sequence shown in SEQ ID NO: 1 or 2 or comprising substantially the same amino acid sequence as the one shown in SEQ ID NO: 1 or 2, which peptide acts as HGF, or a partial polypeptide thereof which can also function as HGF;

(17) Use of the DNA molecule encoding HGF in the manufacture of a medicinal drug for suppressing the fibrosis of a transplanted organ as brought about by the administration of an immunosuppressive drug;

(18) The use as described above under (17), characterized in that the DNA molecule encoding HGF is a DNA molecule consisting of the nucleotide sequence as shown in SEQ ID NO: 3 or 4, or a DNA molecule which hybridizes under stringent conditions with a DNA molecule comprising a nucleotide sequence complementary to the DNA molecule consisting of the nucleotide sequence as shown in SEQ ID NO: 3 or 4 and which encodes a peptide acting as HGF;

(19) The use as described above under any one of (15) to (18), characterized in that the immunosuppressive drug is Tacrolimus;

(20) Use of HGF in the manufacture of a medicinal drug for allowing a recipient patient to acquire immunologic tolerance to a transplanted organ;

(21) The use as described above under (20), characterized in that said HGF is a peptide consisting of the amino acid sequence shown in SEQ ID NO: 2 or comprising substantially the same amino acid sequence as the one shown in SEQ ID NO: 1 or 2, which peptide acts as HGF, or a partial polypeptide thereof which can also function as HGF;

(22) Use of DNA encoding HGF in the manufacture of a medicinal drug for allowing a recipient patient to acquire immunologic tolerance to a transplanted organ; and

(23) The use as described above under (22), characterized in that said DNA is a DNA molecule consisting of the nucleotide sequence as shown in SEQ ID NO: 4, or a DNA molecule which hybridizes under stringent conditions with a DNA molecule comprising a nucleotide sequence complementary to the DNA molecule consisting of the nucleotide sequence as shown in SEQ ID NO: 4 and which encodes a peptide acting as HGF.

As used herein, the term "fibrosis" refers to excessive accumulation in a transplanted organ of extracellular matrix substances, such as collagen fibers, resulting in the morbid conditions of hardening of the transplanted organ, while the term "immunologic tolerance" refers to suppression of destructive actions by the recipient's immune system so that the donor's cells or tissues may not be attacked by the recipient's immune system during organ transplantation.

The Effects of the Invention

The agent for suppressing the fibrosis of a transplanted organ according to the present invention, which acts to suppress the fibrosis of a transplanted organ in an animal having had an organ transplanted which is placed on the long-term immunosuppressant regimen, can prevent the transplanted organ from undergoing gradual fibrosis and also eventually from falling into organ insufficiency.

The immunologic-tolerance acquiring agent of the present invention can be given to a recipient animal (patient) immediately after having had a donor's organ transplanted to thereby allow the recipient animal (patient) to acquire the immunologic tolerance to the transplanted organ, and consequently can suppress rejection to the transplanted organ. The immunologic-tolerance acquiring agent of the present invention can be administered to a transplant-recipient animal to allow the animal to acquire the immunologic tolerance to the donor, thereby enabling such animal to induce the conditions of being thereafter rendered unreactive to any immunologic response to the donor or donor's organ, and can reduce the dose of the immunosuppressive drug or suspend the administration of such drug. In advance of transplantation of an organ, furthermore, the immunologic-tolerance acquiring agent of the present invention can also be administered to a recipient, simultaneously with implantation of a donor's tissue (e.g., a tissue involved in the immunity to be described below) other than the organ to be transplanted, to thereby allow the recipient to acquire the immunologic tolerance to the donor's organ. On the other hand, the immunologic-tolerance acquiring agent of the present invention can also be administered to a donor, simultaneously with implantation of a donor's tissue (e.g., a tissue involved in the immunity to be described below) other than the organ to be transplanted, to thereby allow the donor to acquire the immunologic tolerance to the recipient. By allowing the immunologic tolerance to be acquired by either one of the above-described procedures, it may become possible to perform organ transplantation between the donor and recipient for both of which the organ transplantation has heretofore been infeasible owing to absence or lack of the complex histocompatibility antigen matching. Also, the immunologic-tolerance acquiring agent of the present invention can suppressor reduce rejection after organ transplantation in a recipient having acquired the immunologic tolerance to a donor who has had an organ transplanted from the donor or having had an organ transplanted from the donor who has acquired the immunologic tolerance to the recipient. The above-described suppressed or reduced rejection can permit administration of an immunosuppressive drug or a dose thereof to be suspended or reduced. As used herein, the term "animal" is understood to comprehend mammals inclusive of humans.

THE BEST MODE FOR CARRYING OUT THE INVENTION

Figure 1:
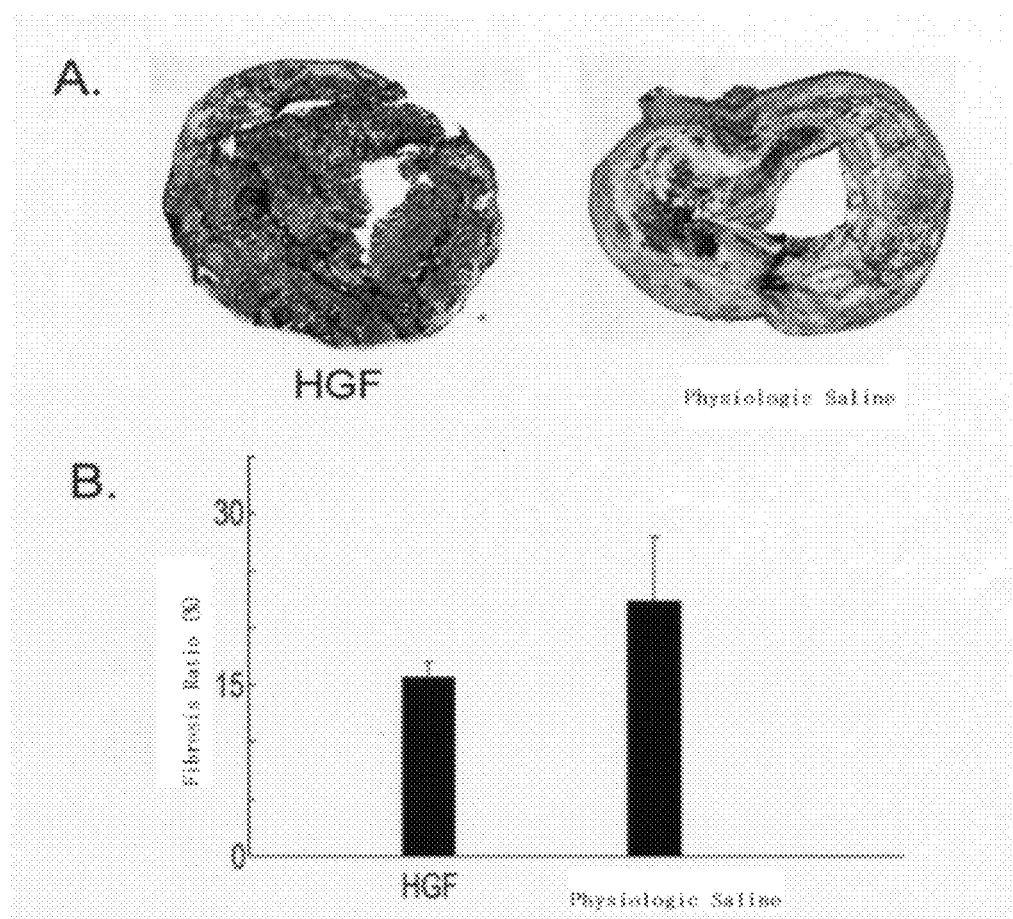
FIG. 1A is a view illustrating the pathological picture of the heart transplanted in the mouse which survived 60 days after transplantation as well as a graph FIG. 1B showing a proportion of the cross-section area of the fibrosis portion to the one of the total cross-section area of the heart wall.
Figure 2:
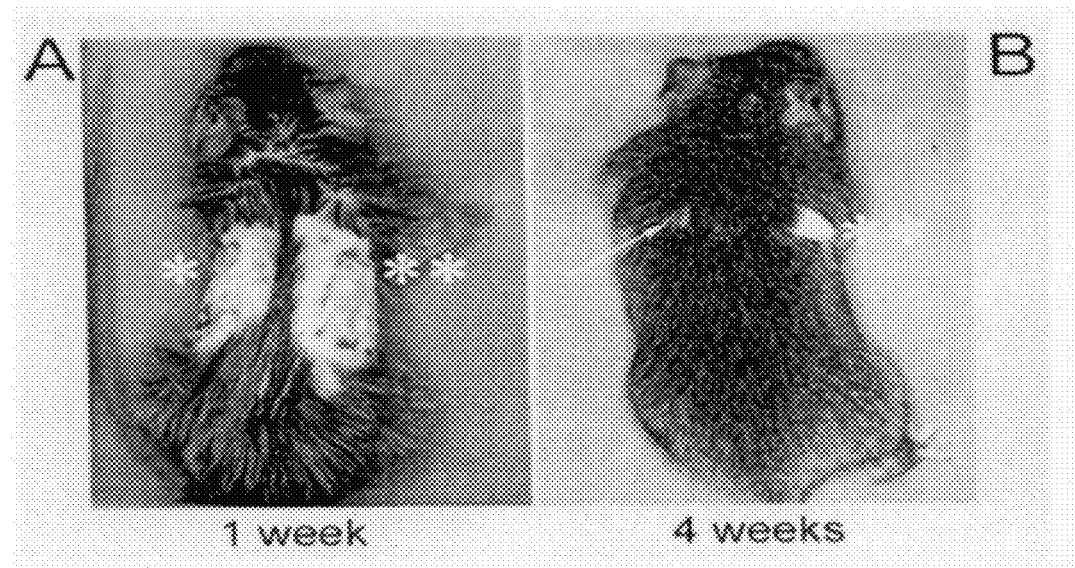
FIGS. 2A-B is a view illustrating the survived graft of a white-haired skin section of a BALB/c mouse implanted onto a black-haired skin section of a C3H/He mouse.

HGF that is usable in the present invention is the known substance, and use can be made of any one of HGFs as prepared by various methods, only if it is purified to such an extent as may be usable as a medicinal drug. Referring to the method for preparing HGF, for example, cells producing HGF in primary culture or as cell line can be cultivated, followed by separation and purification from the supernatant to yield HGF. By following the genetic engineering procedure, alternatively, a gene encoding HGF is inserted into a suitable vector, followed by introduction into a suitable host cell to effect transformation, and the transformant can be cultivated, followed by isolation from the supernatant liquid to give the objective recombinant HGF (for example, refer to the official Gazette of JP No. Hei 5-111382A, Biochem. Biophys. Res. Commun. 1989, vol. 163,p. 967, etc.). The above-described host cell is not particularly limited, and there can be used a variety of host cells as conventionally utilized in the genetic engineering procedure, such as $E.\ coli,$ yeasts or animal cells, etc. HGF variants as obtained by these manners may allow one to a plural number (e.g., several (e.g., 1 to 8); the same is understood to hold true hereinafter)) of amino acids in the amino acid sequence to undergo substitution, deletion or addition, and may allow the sugar chain similarly to undergo substitution, deletion or addition, only if these variants have substantially the same action as the naturally occurring HGF. Such HGF variant may be exemplified by the 5 amino-acids deleted type of HGF to be described below. In this context, the expression "to allow one or a plural number of amino acids to undergo substitution, deletion or addition" as referred to in the amino acid sequence is understood to denote that such a number (one to several) as may be caused through the well known technical procedures, such as the genetic engineering procedure, site-specific mutagenesis procedure, etc., or may occur naturally is allowed to undergo deletion, substitution or addition and others. The expression "HGF having allowed the sugar chain to undergo substitution, deletion or addition" refers to, for example, naturally occurring HGF having had the sugar chain deleted through treatment with enzymes, etc., naturally HGF having allowed the amino acid sequence at the sugar-chain addition site to undergo mutation in such a manner as may not add sugar-chains, or naturally occurring HGF having allowed the amino acid sequence to undergo mutation in such a manner as may add sugar chains to sites different from the site of sugar-chain addition.

Such variant HGF also includes proteins which show amino acid sequences of at least about 80% or more homology with the amino acid sequence of HGF, preferably not less than about 90% homology, more preferably not less than about 95% homology, and can act as HGF. The term "homology" in the above-described amino acid sequence means the degree of agreement or coincidence among the amino acid sequences in terms of amino acid residues constituting individual sequences as found when the primary structures of proteins are compared.

The above-mentioned HGF includes, for example, the amino acid sequences shown by SEQ ID NO: 1 or 2. The variant HGF as represented by the SEQ ID NO: 2 is a 5 amino-acids deleted type of HGF which has 5 amino acid residues deleted at the positions 161 to 165 in the amino acid sequence shown by SEQ ID NO: 1. Both of the proteins possessing the amino acid sequences shown by SEQ ID NOS: 1 and 2, respectively, are naturally occurring HGF of human origin, which elicit mitogen and motogen activities, etc. as HGF.

Peptides comprising substantially the same amino acid sequences as the one shown by SEQ ID NO: 1 or 2 preferably include peptides comprising amino acid sequences of at least about 80% or more homology with the amino acid sequence shown by SEQ ID NO: 1 or 2, preferably not less than about 90% homology, more preferably not less than about 95% homology, such as peptides which are generated by subjecting one to several amino acid residues out of the amino acid sequence shown by SEQ ID NO:1 or 2 to insertion, deletion or substitution with different amino acid residues and which can act as HGF. The amino acids to be inserted or substituted may be non-natural amino acids other than 20 kinds of amino acids encoded by genes. Such non-natural amino acids may be any amino acids, only if they possess amino and carboxyl groups, and may be exemplified by γ-aminobutyric acid, etc.

Such peptides each may be used as a single constituent or as mixtures thereof.

The HGFs which are usable in the present invention may have either one of a carboxyl (—COOH), carboxylate (—COO—), amide (—CONH$_2$) or ester (—COOR) group at the C-terminus. In this context, R as used in the ester group may be exemplified by $C_{1-6}$ alkyl groups, such as methyl, ethyl, n-propyl, isopropyl, n-butyl, etc., $C_{3-8}$ cycloalkyl groups, such as cyclopentyl, cyclohexyl, etc., $C_{6-12}$ aryl groups, such as phenyl, α-naphthyl, etc., $C_{7-14}$ aralkyl groups, such as phenyl-$C_{1-2}$ alkyl groups, e.g., benzyl, phenetyl, etc., or α-naphthyl-$C_{1-2}$ alkyl groups, e.g., α-naphthylmethyl, etc., as well as pivaloyloxymethyl group frequently used as an ester for oral preparations. In cases where the HGF as used in this present invention has carboxyl groups (or carboxylates) at sites other than the C-terminus, the HGF which has its carboxyl group amidated or esterified is also included in the HGF of the present invention, whereby such ester includes the above-mentioned C-terminus ester. Furthermore, the HGF as used in the present invention includes the above-described peptides whose N-terminal methionine residue has its amino group protected with a protective group (e.g., $C_{1-6}$ acyl groups, such as C2-6 alkanoyl groups inclusive of formyl and acety groups, etc.), whose glutamyl group as generated by in vivo truncation of its N-terminal site is converted to pyroglutamic acid, or whose intramolecular amino acid has its side-chain substituent (e.g., —OH, —SH, amino group, imidazole group, indole group, guanidino group, etc.) protected with an appropriate protective group (e.g., acyl groups, such as $C_{2-6}$ alkanoyl groups, inclusive of formyl and acetyl groups, etc.), or conjugated proteins, such as glycoproteins derived through addition of sugar chains to the above-mentioned peptides, and the like.

The partial polypeptides (hereinafter referred to in some instances briefly as "partial polypeptide") of HGF as used in the present invention may be any peptides, only if they are partial polypeptides of the above-described HGFs. Referring to a number of the amino acids of such partial polypeptides in the present invention, preferred are peptides comprising not less than at least about 20 amino acids out of the constituent amino acid sequence of the above-mentioned HGF, preferably not less than about 50 amino acids and more preferably not less than 100 amino acids. The partial polypeptides of the present invention may have any one out of carboxyl (—COOH), carboxylate (—COO—), amide (—CONH$_2$) and ester (—COOR) groups at their C-termini. Furthermore, the partial polypeptides of the present invention, as is the case with the above-mentioned HGF include the peptides having the amino group of their N-terminus methionine residue protected with a protective group, the peptides having Gln as generated by in vivo truncation of their N-terminal side converted to pyroglutamic acid, the peptides whose intramolecular amino acid has its side-chain substitute protected with an appropriate protective group, and conjugated peptides, such as the so-called glycopeptides generated through addition of sugar chains.

Salts of the HGFs and partial polypeptides thereof as used in the present invention may be exemplified by physiologically allowable acid-addition salts with acids or bases, with the physiologically allowable salts, among others, being preferable. Such salts include, for example, salts with inorganic acids (e.g., hydrochloric acid, phosphoric acid, hydrobromic acid, sulfuric acids, etc.), or salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.).

The HGFs and partial polypeptides thereof which are usable in the present invention can be produced in accordance with the known peptide synthesis methods or through truncation of HGF with a suitable peptidase. The peptide synthesis method may be either of the solid-phase and liquid-phase synthesis methods. Thus, a partial polypeptide or amino acids which constitutes HGF can be allowed to condensate with the remaining portion, followed by elimination of any protective groups from the condensate, if such groups exist, to thereby yield the objective peptide. The known condensation and protective-group elimination procedures include, for examples, the procedures and methods as described M. Bodanszky and M. A. Ondetti, Peptide Synthesis, Interscience Publishers, New York (1966), Schroeder and Luebke, The peptide, Academic Press, new York (1965) (1965), etc. After completion of the reaction, the ordinarily employed purification methods, such as solvent extraction, distillation, column chromatography, liquid chromatography, recrystallization, etc., can be combined to isolate and purify the partial polypeptide of the HGFs. When the partial polypeptide as obtained by the above-described methods is in the free form, such peptide can be converted to a suitable salt by the known procedure, or conversely when the partial polypeptide is in the form of a salt, the known procedures can be used to convert the same to a free form.

In the present invention, the HGF encoding DNA molecules can be contained as an active ingredient.

The DNA molecule encoding HGF includes, for example, DNA molecules comprising the nucleotide sequence as shown by SEQ ID NO: 3 or 4, or DNA molecules which hybridize under stringent conditions with a DNA molecule comprising a nucleotide sequence complementary to the DNA molecule consisting of the nucleotide sequence as shown by SEQ ID NO: 3 or 4 and which encode the protein showing activities substantially equivalent to those of HGF, such as mitogen and motogen activities. In this context, the DNA molecule, which hybridizes with the DNA molecule consisting of the nucleotide sequence as shown by SEQ ID NO: 3 or 4, denotes DNA molecules obtained by colony hybridization, plaque hybridization or Southern blot hybridization and the like with use of the above-described DNA molecule as a probe. Specifically, there can be mentioned, for example, the DNA molecule identified by carrying out hybridization at a temperature of about 65° C. in the presence of sodium chloride of a concentration in the range of about 0.7 to 1.0 M with use of a filter having a colony- or plaque-derived DNA molecule immobilized thereto, and subsequently washing the filter with an SSC solution (SSC solution having one-fold or standard concentration is composed of 150 mM of sodium chloride and 15 mM of sodium citrate) having about 0.1- to 2-fold concentration.

Specific examples of the DNA molecule, which hybridizes with DNA consisting of the nucleotide sequence shown by SEQ ID NO: 3 or 4 as described above, include DNA molecules showing not less than about 80% of homology with the nucleotide sequence shown by SEQ ID NO: 3 or 4, preferably not less than about 90% homology and more preferably not less than about 95% homology. Hybridization can be conducted in accordance with the known procedures, such as the procedures described in Molecular Cloning, A Laboratory Manual, Third Edition (J. Sambrook et al., Cold Spring Harbor Lab. Press, 2001: hereinafter referred to briefly as "Molecular Cloning $3^{rd}$ Edition"). When a commercially available library is used, hybridization can be carried out in accordance with the procedure described in Instruction Manual as attached thereto.

Furthermore, the DNA molecule encoding HGF of the present invention is not limited to the above-described ones, and any DNA molecules can be used as the DNA molecule encoding HGF, insofar as the expressed proteins exhibit substantially the same activities as HGF. For example, the DNA molecules encoding partial polypeptides of HGF also fall into the scope of the present invention, only if they encode the partial polypeptide which can act as HGF. The DNA molecule encoding the partial polypeptide of HGF may be any DNA molecules, only if they comprise the nucleotide sequence encoding the above-described partial polypeptide. As is the case with the above-described DNA molecule encoding HGF, additionally, it may be any one of genomic DNA, genomic DNA library, the above-described cell/tissue derived cDNA, the above-described cell/tissue derived cDNA library, and synthetic DNA molecules. The vector to be used in the library maybe any one of bacteriophages, plasmids, cosmids and phagemids. The mRNA fraction as prepared from the above-described cells/tissues can be used to make amplification directly by the RT-PCR. Specific examples of the DNA molecule encoding the partial polypeptide of the present invention include (a) DNA molecules comprising fractional nucleotide sequences of the DNA consisting of the nucleotide sequence as shown by SEQ ID NO: 3 or 4, (b) DNA molecules which hybridize under stringent conditions with a DNA molecule comprising nucleotide sequence complementary to a DNA molecule comprising a fragmental nucleotide sequence of the DNA molecule consisting of the nucleotide sequence as shown by SEQ ID NO: 3 or 4, or (c) DNA molecules comprising the fragmental nucleotide sequence as described above under (a) or (b), and the like.

The DNA can be readily obtained, for example, by the ordinary hybridization and PCR, etc., specifically by consulting with the reference books, such as the previously described Molecular Cloning, etc.

The RNA molecules encoding the HGF or partial polypeptides thereof which are usable in the present invention can also be used in the present invention and fall into the scope of the present invention, if such RNA molecules are capable of expressing such HGF or partial polypeptides thereof by reverse transcriptases. Such RNA molecules can be obtained by the known procedures, as well.

The agent for suppressing the fibrosis of a transplanted organ or immunologic-tolerance acquiring agent according to the present invention can be applied to humans, as well as mammals (e.g., cows, horses, pigs, sheep, dogs, cats, etc.).

The organs to which the agent for suppressing the fibrosis of a transplanted organ can be applied include, for example, the heart, kidney, liver, small intestine, pancreas, skin or corneum, with the heart among others being preferable. Also, the immunologic-tolerance acquiring agent of the present invention is also applicable to the transplantation of hematopoietic cells, in addition to the above-mentioned organ transplants.

The agent for suppressing the fibrosis of a transplanted organ or immunologic-tolerance acquiring agent according to the present invention can assume various dosage forms, such as liquid preparations, solid preparations or capsules, etc., wherein HGF alone or together with conventionally used carrier is generally processed into an injectable solution, inhalant, suppository or oral preparation. The above-mentioned injectable solution may be either aqueous or oily injectable solution. In the case of manufacture of an aqueous injectable solution, such aqueous injectable solution can be prepared in accordance with the known process by appropriately admixing an aqueous solvent (e.g., water for injection uses, purified water, etc.) with pharmaceutically allowable additives, such as isotonic agent (e.g., sodium chloride, potassium chloride, glycerol, mannitol, sorbitol, boric acid, borax, glucose, propylene glycol, etc.), buffering agent (e.g., phosphate buffer, acetate buffer, borate buffer, carbonate buffer, citrate buffer, tris-buffer, glutamate buffer, ϵ-aminocaproate buffer, etc.), preservative (e.g., methyl p-oxybenzoate, ethyl p-oxybenzoate, propyl p-oxybenzoate, butyl p-oxybenzoate, chlorobutanol, benzyl alcohol, benzalkonium chloride, sodium dehydroacetate, sodium edetate, boric acid, borax, etc.), thickening agent (e.g., hydroxymethyl cellulose, hydroxypropyl cellulose, polyvinyl alcohol, polyethylene glycol, etc.), stabilizer (e.g., sodium hydrogen sulfite, sodium thiosulfate, sodium edetate, sodium citrate, ascorbic acid, dibutyl hydroxytoluene, etc.) or pH regulating agent (e.g., hydrochloric acid, sodium hydroxide, phosphoric acid, acetic acid, etc.), and dissolving HGF in the resultant solution, followed by sterilization by filtration through a filter and filling into a sterile container. Also, use is made of a suitable solubilizing agent, such as alcohols (e.g., ethanol, etc.), polyhydric alcohols (e.g., propylene glycol, polyethylene glycol, etc.) or a nonionic surfactant (e.g., Polysorbate 80, polyoxyethylene hardened castor oil 50, etc.), and the like. In cases where an oily injectable solution is produced, there can be used an oily solvent, such as sesame oil or soybean oil, etc., while use maybe made of a solubilizing agent, such as benzyl benzoate or benzyl alcohol, etc. The injectable solution as prepared is ordinarily filled into a suitable ampoule or vial. The content of HGF in the injectable solution is generally adjusted to a level in the range of about 0.0002 to 0.2% in w/v, preferably in the range of about 0.001 to 0.1% in w/v. The liquid preparations, inclusive of injectable solutions, etc., are preferably stored through freezing or lyophilization, etc. to remove the moisture. The lyophilisate is used by adding distilled water for injection, etc. for reconstitution.

An oral preparation may be exemplified by such dosage forms as a tablet, granule, fine granule, powder, capsule, liquid preparation, emulsion, suspension or syrup, etc. such dosage forms are produced by the known processes. In cases where the granule or tablet is manufactured, such dosage form is produced by using pharmaceutically allowable additives, such as an excipient (e.g., lactose, white sugar, glucose, starch, crystalline cellulose, etc.), lubricant (e.g., magnesium stearate, talc, stearic acid, calcium stearate, etc.), disintegrant (e.g., starch, sodium carmellose, calcium carbonate, etc.) or binder (e.g., starch paste solution, hydroxypropylcellulose solution, carmellose solution, gum-arabic solution, gelatin solution, sodium-alginate solution, etc.), while the granule or tablet may be provided with a coating film by use of a suitable coating agent (e.g., gelatin, white sugar, gum arabic, carnauba wax, etc.) or enteric coating agent (e.g., cellulose acetate phthalate, methacrylic-acid copolymers, hydroxypropylcellulose phthalate, carboxymethyl ethylcellulose, etc.), etc. In the case of manufacture of a capsule, suitable use is made of the known excipients, magnesium stearate, calcium stearate, talc or light anhydrous silicate for the purpose of enhancing the fluidity and lubricating property, crystalline cellulose and lactose for the purpose of increased pressurized fluidity, or the above-mentioned disintegrant, and the like. HGF may be mixed uniformly with the above-mentioned excipient or granulated, or the granule as granulated is provided with a coating film by use of a suitable coating agent, followed by filling into a capsule or enclosure-molding with a capsule base as plasticized by adding glycerol or sorbitol, etc. to a suitable capsule base (e.g., gelatin, etc.). Such capsules can be incorporated with a coloring agent or preservative (e.g., sulfur dioxide, methyl p-oxybenzoate, ethyl p-oxybenzoate, propyl p-oxybenzoate, butyl p-oxybenzoate, etc.), and the like. Such capsules can be provided in the forms of an ordinary capsule, as well as an enteric-coating capsule, gastric-resistant capsule or release-controlled capsule. In the case of the enteric capsule, HGF coated with an enteric coating agent or HGF after being admixed with a suitable excipient is filled into an ordinary capsule. Alternatively, HGF or HGF admixed with the above-mentioned excipient can be filled into a capsule coated with an enteric coating agent or a capsule molded with an enteric polymer used as a base. In cases where a syrup is produced, there can be appropriately selected and used, for example, a stabilizer (e.g., sodium edentate, etc.), suspending agent (e.g., gum arabic, carmellose, etc.), flavoring agent (e.g., simple syrup, glucose, etc.) or fragrance, etc.

A suppository can also be prepared by the ordinary pharmaceutical-preparation process with use of the conventionally used base (e.g., cacao fat, laurin fat, glycerogelatin, macrogol, whittep sol, etc.).

Also, an inhalant can be prepared by the conventional pharmaceutical-preparation means, and in the case of manufacture of such inhalant, the additives to be used may be any additives which are used in the inhalant preparation, and there are used, for example, a propellant as well as the above-described excipient, binder, lubricant, preservative, stabilizer, isotonic agent, pH regulating agent or flavoring agent (e.g., citric acid, menthol, ammonium glycyrrhizate, glycine, fragrance, etc.) and the like. As a propellant, use is made of liquefied gas propellants or compressed gases, etc. The liquefied gas propellant may be exemplified by fluorinated hydrocarbons (replacement Freons, such as HCFC22, HCFC-123, HCFC-134a, HCFC142, etc. and the like), liquefied petroleum gas, dimethyl ether, and the like. The compressed gas includes, for example, soluble gases (e.g., carbon dioxide gas, nitrogen suboxide gas, etc.), or insoluble gases (e.g., nitrogen gas, etc.), and the like.

HGF as usable in the present invention, together with a biodegradable polymer, can be processed into the controlled-release preparation. HGF, especially when processed into a controlled-release preparation, can be expected to produce the beneficial effects, such as sustained maintenance of the blood level, reduction of the number of administration and alleviation of side effects, etc. The said controlled-release preparation can be produced, for example, in accordance with the known process as described in Drug Delivery System, Chapter 3 (published by CMC, 1986).

The in vivo degradable polymer which is used in the controlled release preparation can be appropriately selected among the known in vivo degradable polymers, and may be exemplified by polysaccharides, such as starch, dextran or chitosan, etc., proteins, such as collagen or gelatin, etc., polyamino acids, such as poly(glutamic acid), polylysine, polyleucine, polyalanine or polymethionine, etc., polyesters, such as poly(lactic acid), poly(glycolic acid), polymer or copolymer of lactic acid/glycolic acid, polycaprolactone, poly-(β-hydroxybutyric acid), poly (malic acid), polyacid anhydride or copolymer of fumaric acid/polyethylene glycol/vinyl-pyrrolidone, polyalkylcyanoacrylic acids, such as poly-orthoesters or poly(methyl α-cyanoacrylate), polycarbonates, such as polyethylene carbonate or polypropylene carbonate, etc., and the like, with polyesters being preferable and poly(lactic acid) or polymers or copolymers of lactic acid/glycolic acid being more preferable. In the case of use of the polymer or copolymer of lactic acid/glycolic acid, its composition ratio (lactic acid/glycolic acid) (mole %) varies with the length of time of the controlled release, and ranges from about 100/0 to 50/50, in cases where the length of time of controlled release is, for example, about 2 weeks to 3 months, preferably about 2 weeks to one month. The said polymer or copolymer of lactic acid/glycolic acid generally shows a weight-average molecular weight of about 5,000 to 20,000. The copolymer of lactic acid/glycolic acid can be produced, for example, by the known production process, such as the one described in the Official Gazette of JP Sho 61-28521 A. The formulation ratio of the in vivo biodegradable polymer to HGF is not particularly limited, and HGF is for example in the range of about 0.01 to 30w/w % against the in vivobiodegradable polymer.

The content of HGF in each of the above-described dosage forms can be suitably adjusted depending upon the dosage form, disease to be treated, severity of the disease or patient's age, etc.

DNA encoding HGF can be administered to a patient in accordance with the conventionally employed methods, such as the ones described in "*Jikken Igaku*" (Experimental Medicine), an extra number entitled "Fundamental Techniques of Gene Therapy", published by Yohdo-sha in 1996, "*Jikken Igaku*" (Experimental Medicine), an extra number entitled "Experimental Methods of Gene Transfer & Expression Analysis", published by Yohdo-sha in 1997, and Handbook of Developmental Research on Gene Therapy, edited by Japanese Society of Gene Therapy, published by N.T.S. in 1999, and the like.

The dosage form can assume any known forms being suited for each of the above-described mode of administration. In the case of a microcapsule, for example, the core substance of host cells having the HGF-encoding DNA or the expression plasmid containing the HGF-encoding DNA transfected therein is covered with the known coating-film substance in accordance with the known method (e.g., coacervation method, interfacial polymerization method or double-nozzle method, etc.) to produce such microcapsule in the form of a microparticle of about 1 to 500 μm in diameter, preferably about 100 to 400 μm, whereby the coating-film substance includes, film-forming polymers, such as Carboxymethylcellulose, cellulose acetate phthalate, ethyl-cellulose, alginic acid or its salts, gelatin, gelatin/gumarabic, nitrocellulose, polyvinyl alcohol or hydroxypropylcellulose, poly(lactic acid), poly(glycolic acid), chitosan-alginate, cellulose sulfate-poly(dimethyldiallyl)-ammonium chloride, hydroxyethyl methacrylate/methyl methacrylate, chitosan-carboxymethylcellulose, alginate-polylysine-alginate, etc.

The content of DNA in the preparation can be appropriately adjusted depending upon the disease to be treated, the patient's age and weight, etc., and its daily dose ordinarily ranges from about 0.0001 to 100 mg as DNA of the present invention, preferably from about 0.001 to 10 mg.

Also, the HGF-encoding DNA and HGF can be used independently and both can be utilized concomitantly, as well.

The immunosuppressive drug is understood to comprehend all the immunosuppressive drugs which are usable in the organ transplantation. Such immunosuppressive drug includes, for example, Cyclosporin and Tacrolimus (FK506) which act as a inhibitor against calcineurin; Zenapax and Simulect which belong to the IL-2 antibody; Rapamycin, an inhibitor against TOR (target of rapamycin: a factor which constitutes the signal transduction pathway for modifying the physiologic functions involved in cellular growth in response to the conditions of nutrition), etc.; CellCept which is an antimetabolite, and the like. The agent for suppressing the fibrosis of a transplanted organ according to the present invention is useful, among others, for the prevention, amelioration or therapy of the fibrosis of a transplanted organ as caused by the long-term administration of Tacrolimus.

Also, the agent for suppressing the fibrosis of a transplanted organ or immunologic-tolerance acquiring agent according to the present invention may appropriately be incorporated with other medicinal active ingredients, unless contrary to the objects of the present invention. Such medicinal active ingredient maybe exemplified by coronary vasodilators (e.g., amyl nitrite, isosorbide nitrate, nitroglycerin, trapidil, etc.), β-blockers (e.g., oxprenolol, carteolol, bucumolol, bufetolol, propranolol, pindolol, etc.), calcium antagonists (e.g., diltiazem, verapamil, nifedipine, nicardipine, etc.), peripheral circulation disorder remedies (e.g., alprostadylalfadex, kalidinogenase, tocopherol, nicomol, etc.), antiarrhythmic drugs (e.g., ajmarine, procainamide, lidocaine, etc.), antihypertensive drugs (e.g., furosemide, trichlormethiazide, hydralazine, sympathomimetics depressant drugs, calcium blockers, etc.), antihyperlipemic drugs (e.g., clofibrate, pravastatin, simvastatin, lovastatin, nicomol, etc.), anticoagulant drugs (e.g., heparin, warfarin, dicumarol, aspirin, etc.), thrombolytic drugs (e.g., urokinase, etc.), antidiabetic drugs (e.g., tolubutamide, chlorpropamide, acetohexamide, glibenclamide, metformin, acarbose, etc.), anti-inflammatory drugs (e.g., diclofenac sodium, ibuprofen, indomethacin, etc.), antimicrobial drugs (e.g., cefixime, cefdinir, ofloxacin, tosufloxacin, etc.) or antifungal drugs (e.g., fluconazole, itraconazole, etc.), and the like. The pharmaceutical preparations containing such medicinal active ingredients can be used concomitantly with the preparations of the present invention. Such medicinal active ingredients are not particularly limited, insofar as the object of the present invention can be attained, and can be used in appropriate formulation proportions or concomitant-use proportions.

The agent for suppressing the fibrosis of a transplanted organ according to the present invention can be administered to a patient through a suitable route of administration according to their dosage forms. For example, the agent can be processed into a dosage form of an injectable solution for the intravenous, intraarterial, subcutaneous or intramuscular injection. The dose maybe appropriately adjusted depending upon the symptoms, age or weight of a patient, etc., and ordinarily ranges from about 0.001 to 1000 mg as HGF per adult patient, preferably from about 0.01 to 100 mg, which can be suitably given to a patient once a day or as divided into several times a day. Also, the agent for suppressing the fibrosis of a transplanted organ according to the present invention is desirably administered to a patient simultaneously with, before or immediately after, administration of an immunosuppressive drug after organ transplantation. Furthermore, the agent for suppressing the fibrosis of a transplanted organ according to the present invention may start be administered to a patient in advance of organ transplantation.

The immunologic-tolerance acquiring agent of the present invention is administered to a recipient patient simultaneously with, before or after, organ transplantation, and referring to the term of administration, the said immunologic-tolerance acquiring agent is desirably administered to the patient for at least two weeks after organ transplantation. Prior to organ transplantation, furthermore, it is desirable to transplant a donor animal's tissue different from the organ transplant, for example, the donor animal's lymphocytes in the case of transplantation of the heart, into a recipient animal to thereby administer to the recipient animal the immunologic-tolerance acquiring agent of the present invention together with an immunosuppressive drug for at least about two weeks. Prior to organ transplantation, alternatively, a recipient's tissue, such as lymphocytes, etc., is transplanted into a donor for organ transplantation, and then the immunologic-tolerance acquiring agent of the present invention is given to the donor together with an immunosuppressive drug to thereby enable the donor's organ to acquire the immunologic tolerance to the recipient. By following the latter procedural technique, the donor's organ which has acquired the immunologic tolerance to the recipient can be transplanted into the recipient to thereby permit the recipient to suppress the rejection reaction of the transplanted organ.

The immunologic-tolerance acquiring agent of the present invention can be administered to a patient through a suitable route of administration by an appropriate method of administration at doses, as is the same with the agent for suppressing the fibrosis of a transplanted organ according to the present invention.

The term "tissue" as mentioned above in the donor's tissues or recipient's tissue refers to the tissues involved in the immunity, inclusive of the organs and tissues, such as the bone marrow, thymus, spleen, lymph nodes, tonsils, blood vessels, skin, intestinal tracts, etc., or the immunocytes, such as leucocytes, macrophage, lymphocytes (NK (natural killer) cell, helper T-cell, killer T-cell, B cell), dendritic cells, etc., cytokines, antibodies (immunoglobulins (Ig), IgG, IgA, IgM, IgD, IgE, etc.), granulocytes (neutrophils, eosinophils and basophils), and the like.

To be described below are the present invention by way of the examples, but the present invention is not understood to be limited thereto.

In the examples, the term "%" denotes "% by mass", unless particularly specified otherwise, and HGF used was the variant HGF (whose nucleotide sequence is shown by SEQ ID NO: 2) having had 5 amino acids deleted.

EXAMPLE 1

Suppressory Effect on the Fibrosis of the Cardiac Muscle in a Mouse Having the Heart Transplanted (1) Generation of a Heart Transplanted Model:

Used were 8-weeks aged, male mice weighing ca. 20 g of two species (BALB/c and C3H/He mice). A BALB/c mouse used as a donor animal were kept under anesthesia with the mixed drug of ketamine (100 μg/kg) and xylazine (10 μg/kg), and the heart was subjected to perfusion with 1 mL of physiologic saline supplemented with 7.5% by mass of heparin and removed through excision to use as the heart for transplantation. A C3H/He mouse was maintained under anesthesia with the mixed drug consisting of ketamine (100 μg/kg) and xylazine (10 μg/kg), then subjected to laparotomy and allowed to undergo heterotopic transplantation of the heart for transplantation excised from the BALB/c mouse into the abdomen between the abdominal aorta and abdominal inferior venae cava under microscope.

(2) Administration of Immunosuppressive Drug and HGF

As an immunosuppressive drug, use was made of Prograf-Injectable Solution 5 mg (containing 5 mg/ml of Tacrolimus; manufactured by Fujisawa Pharmaceutical Co.).

Immediately after the transplantation as described above under (1), Tacrolimus was given subcutaneously to the mouse at a dose of 0.1 mg/kg/day once a day for 60 consecutive days with use of a Gauge 27 needle for injection. Immediately after the transplantation, additionally, a solution (0.2 mL; 250 μg of HGF/kg) as prepared by dissolving 1 mg of HGF in 20 mL of physiologic saline was given to animals of the group treated through administration of HGF at the regular interval of 12 hours (500 μg/kg/day) for 14 consecutive days, while the control animals were treated similarly through subcutaneous administration of physiologic saline (0.2 mL) for 14 consecutive days using a Gauge 27 needle for injection.

(3) Histopathological Analysis

While taking as Day 0 the day when the transplantation surgery was performed, the transplanted heart was incised on Day 14, and was fixed in formalin and embedded in paraffin in accordance with the conventional procedure to thereby prepare the heart tissue slices. The tissue slices were Masson-trichrome stained. The stained tissue images were loaded into a computer with a microscopic CCD camera (manufactured by Olympus Co.), and the NIH software package for analysis of images (free software) was used to calculate a surface-area ratio of the fibrosed green-stained section to the total area of the coronary cross-section image of the transplanted heart.

(4) Results

In the control group of animals, the fibrosis-formation ratio of the transplanted heart was shown to be 22.3±7.7% in, whereas it was found to be suppressed at a level as low as 15.6±1.3% in the group treated through administration of HGF (refer to FIG. 1).

This demonstrated that the recombinant human HGF can suppress the fibrosis of the transplanted heart.

EXAMPLE 2

Acquisition of Immunologic Tolerance

Method:

In the same manner as described under (1) of Example 1, using a BALB/c mouse as a donor animal, the heart was transplanted from the BALB/c mouse to a C3H/He mouse in the abdomen between the abdominal aorta and abdominal inferior venae cava. Immediately after the transplantation, a solution (0.2 mL; 250 μg of HGF/kg) as prepared by dissolving 1 mg of HGF in 20 mL of physiologic saline started, and continued, being administered subcutaneously to the animals at the regular interval of 12 hours (500 μg/kg/day) for 14 consecutive days with use of a Gauge 27 needle for injection. The survived mouse 60 days after the transplantation was subjected to skin excision from the back, followed by transplantation of a 1-cm$^2$ skin piece removed from a BALB/c or C57BL/10 mouse into the skin-excised portion.

Results:

In the C3H/He mouse, which had survived for 60 days after transplantation of the heart, followed by transplantation of a piece of the back skin from the donor animal of the BALB/c mouse, it was found that the transplanted white-haired skin piece of BALB/c mouse had been able to be implanted successfully on the black-haired skin of the BALB/c mouse. This finding demonstrates that the C3H/He mouse having the heart transplanted from the BALB/c mouse acquired the immunologic tolerance to the BALB/c mouse.

INDUSTRIAL APPLICABILITY

The agent for suppressing the fibrosis of a transplanted organ and immunologic-tolerance acquiring agent according to the present invention are useful in the fields of organ transplantation and regeneration therapy.

The invention claimed is:

1. A method for suppressing fibrosis caused by long-term administration of an immunosuppressive drug in a mammal having had an organ transplanted and having been placed on a long-term immunosuppressant regimen, comprising administering a hepatocyte growth factor (HGF) consisting of an amino acid sequence having not less than about 95% homology with SEQ ID NO: 2 to said mammal, wherein administration of said HGF is simultaneous with or immediately after administration of said immunosuppressive drug, and wherein the HGF suppresses the development of fibrosis caused by said immunosuppressive drug in the transplanted organ.

2. The method according to claim 1, wherein the HGF is a peptide consisting of the amino acid sequence shown in SEQ ID NO: 1 or SEQ ID NO: 2.

3. The method according to claim 1, wherein the immunosuppressive drug is Tacrolimus.

* * * * *